United States Patent
Sumetsky (10) Patent No.: US 8,860,935 B2
(45) Date of Patent: Oct. 14, 2014

(54) HIGH Q-FACTOR CONICAL OPTICAL MICRORESONATOR AND UTILIZATION IN THE LOCATION CHARACTERIZATION OF OPTICAL FIBERS

(75) Inventor: Mikhail Sumetsky, Bridgewater, NJ (US)

(73) Assignee: OFS Fitel, LLC, Norcross, GA (US)

(*) Notice: Subject to any disclaimer, the term of this patent is extended or adjusted under 35 U.S.C. 154(b) by 0 days.

(21) Appl. No.: 13/822,925

(22) PCT Filed: Sep. 16, 2011

(86) PCT No.: PCT/US2011/051879
§ 371 (c)(1),
(2), (4) Date: Mar. 13, 2013

(87) PCT Pub. No.: WO2012/037432
PCT Pub. Date: Mar. 22, 2012

(65) Prior Publication Data
US 2013/0176557 A1    Jul. 11, 2013

Related U.S. Application Data

(60) Provisional application No. 61/383,900, filed on Sep. 17, 2010, provisional application No. 61/405,172, filed on Oct. 20, 2010.

(51) Int. Cl.
G02B 6/26 (2006.01)
G01N 21/84 (2006.01)
G01N 21/77 (2006.01)

(52) U.S. Cl.
CPC .............. G02B 6/26 (2013.01); G01N 21/7746 (2013.01)

USPC .............................. 356/73.1; 385/16; 385/28

(58) Field of Classification Search
CPC .............................. G02B 6/26; G01N 21/7746
USPC ............ 356/73.1, 246; 385/12, 16, 28, 32, 50
See application file for complete search history.

(56) References Cited

U.S. PATENT DOCUMENTS

| | | | |
|---|---|---|---|
| 7,684,664 B2* | 3/2010 | Digonnet et al. | 385/16 |
| 7,933,022 B2* | 4/2011 | Smith et al. | 356/480 |
| 8,520,988 B2* | 8/2013 | Digonnet et al. | 385/16 |
| 2006/0062508 A1* | 3/2006 | Guo et al. | 385/12 |
| 2010/0158439 A1* | 6/2010 | Koch et al. | 385/28 |
| 2010/0231903 A1* | 9/2010 | Sumetsky | 356/246 |
| 2011/0019186 A1* | 1/2011 | Himmelhaus et al. | 356/317 |

* cited by examiner

*Primary Examiner* — Sang Nguyen
(74) *Attorney, Agent, or Firm* — Law Office of Wendy W. Koba (57) ABSTRACT

A conically tapered optical fiber with a small half-angle γ (e.g., less than $10^{-2}$) has been found able to support whispering gallery mode (WGM) resonances and can therefore be used to form a high-Q cavity. This finding has led to the ability to measure angstrom-level variations in the radius of an optical fiber by viewing the resonance spectrum at various locations where a sensor contacts an optical fiber being measured. An evaluation process is proposed where a microfiber sensor is brought into contact with a target fiber and the created WGM resonance is measured so that location radius variation can be characterized. The sensor is then removed from the target fiber and re-positioned to contact the fiber to another location to repeat the evaluation.

7 Claims, 5 Drawing Sheets

HIGH Q-FACTOR CONICAL OPTICAL MICRORESONATOR AND UTILIZATION IN THE LOCATION CHARACTERIZATION OF OPTICAL FIBERS

CROSS-REFERENCE TO RELATED APPLICATIONS

This application claims the benefit of U.S. Provisional Application 61/383,900, filed Sep. 17, 2010 and U.S. Provisional Application 61/405,172, filed Oct. 20, 2010, both of which are herein incorporated by reference.

TECHNICAL FIELD

The present invention relates to optical microresonators and, more particularly, to a conical microresonator for supporting high Q-factor whispering gallery modes (WGMs) at selected wavelengths and a method that allows for the determination of local variation in radius of an optical fiber from the study of the created WGM resonances.

BACKGROUND OF THE INVENTION

Continuing interest in optical whispering gallery mode (WGM) microresonators can be attributed to their outstanding light confinement properties in applications ranging from atomic physics to optical communication systems. In general, WGMs are optical resonances created within circular structures where the optical signal travels around the circumference of the structure, undergoing repeated internal reflections at near-grazing incidence. The leakage of light can be very small in these structures, leading to high intrinsic quality factors (Q factors). The Q factor is generally defined as a measure of energy loss relative to the energy stored in a resonator (or any type of oscillating device), characterized by the center frequency of a resonance divided by its bandwidth. A "high Q" resonator is therefore associated with a relatively narrow and sharp-peaked resonance feature. These WGM microresonators typically take the form of disks, spheroids or toroids, and have an exceptionally high Q-factor as a result of the strong localization of the circulating signal.

It has previously been shown that WGMs can be excited in a silica microsphere by the evanescent coupling of light from a narrow, tapered fiber (defined as a "sensor" fiber) that is placed in contact with the microsphere. Similarly, WGMs can be excited in a second ("target") fiber by the same contact method with a sensor fiber. Since the round-trip phase change must be an integer multiple of $2\pi$, WGMs only exist at discrete wavelengths as determined by the diameter of the target fiber. The local diameter of a target optical fiber can therefore be deduced from the sensor's transmission spectrum, in which the wavelengths of the target fiber's WGMs appear as coupling resonances (dips) in an output spectrum. The sharpness of the resonance allows for a high resolution measurement to be made.

A prior technique of using WGMs to monitor radius variation in optical fibers required the sensor fiber to be slid along the target fiber. The physical act of moving one fiber along another was found to create problems, such as the collection of microparticles by the sensor fiber, that altered the transmission power and thus corrupted the measurement. The microparticles were also found to scratch the surface of the target fiber. A certain amount of "stick-slip" friction was also encountered.

Thus, there exists a need for an improved technique of characterizing local variations in optical fiber radius utilizing WGM monitoring without introducing the errors and corruption in results associated with the prior art method of sliding the sensor fiber along the target fiber.

SUMMARY OF THE INVENTION

The present invention relates to optical microresonators and, more particularly, to a conical microresonator for supporting high Q-factor WGMs at selected wavelengths and a method that allows for the determination of local variation in the resonant characteristics of an optical fiber from an analysis of a shift in wavelength of the created WGM resonances. Such characteristics can depend on the optical path length of the resonant, which depends on the physical dimensions and the optical properties (e.g., refractive index) of the resonator.

In accordance with the present invention, a conically tapered optical fiber with a small half-angle $\gamma$ (e.g., less than $10^{-2}$ radians) has been found to support WGMs and, therefore, can be used to form a high-Q cavity. One application of a conical optical microresonator is associated with observing variations in the radius of an optical fiber. Angstrom-level variations in the radius of an optical fiber can be thought of as forming a conically tapered fiber. By creating a contact between a localized optical source (such as a tapered microfiber, planar optical fiber, free space propagating optical signal, or the like) and the conically tapered optical fiber, the resonance spectrum associated with the created WGMs can be evaluated to measure the variation in radius at different locations along the length of the optical fiber being measured.

In one aspect, the present invention discloses a high Q-factor optical microresonator comprising a conical optical waveguide with a half-angle $\gamma$, where to support localized whispering gallery modes (WGMs), $\gamma$ satisfies the relation $\gamma \ll \pi^{-3/2}(\beta r)^{-1/2}$. The term r is defined as the local radius of the conical optical waveguide and $\beta$ is a propagation constant defined by $\beta = 2\pi n_r/\lambda$, with $\lambda$ defined as an optical signal propagating along an optical axis of the optical microresonator and $n_r$ defined as the refractive index of the conical optical waveguide. The optical microresonator further comprises a localized optical source that is disposed in contact with the conical optical waveguide and used for excitation of WGMs in the conical optical waveguide.

In general, both the radius and refractive index of the resonator can vary. In that case, the conical waveguide can be formed by axial variation of the physical radius of the optical fiber, as well as by an axial variation of the refractive index. The developed theory can be applied to this compound situation simply by replacing the above-defined conical angle $\gamma$ by an effective conical angle $\gamma_{\textit{eff}}$, defined as follows:

$$\gamma_{\textit{eff}} = \gamma + \gamma_{\textit{ind}}(r_o/n_0),$$

where $\gamma$ is the half-angle of the physical fiber dimension (i.e., the slope of the fiber surface in the axial dimension, as defined above), $\gamma_{\textit{ind}}$ is defined as the slope of the index variation, and $n_0$ is is the refractive index of the optical microresonator. Further, the refractive index of the fiber exhibits a local linear variation in the axial z direction, represented as follows:

$$n(z) = n_0 + \gamma_{\textit{ind}} \times z.$$

In an analogous sense, the device can be considered to be responsive to the effective fiber radius, which depends on both the physical radius and the refractive index properties of the fiber.

The application of the properties of a conic resonator to the investigation of the local slope of an optical fiber, has been found to provide a unique approach for extremely accurate local characterization of optical fibers (which usually have a half-angle γ of $10^{-2}$ or less) and a new paradigm in the field of high Q-factor resonators.

It is an aspect of the present invention that the recognition of the ability of a conically tapered optical fiber to support WGMs has provided for an extremely accurate method of monitoring the variation of radius in an optical fiber at the angstrom level, allowing for the quality of fabricated optical fibers to be assessed quickly and efficiently.

Additionally, a discrete contact measurement process is proposed, where as opposed to the sliding method of the prior art, a sensor in the form of a localized optical source (e.g., tapered microfiber) is brought into contact with a target fiber, the created WGM resonance is observed, and then the sensor is removed from the target fiber. The removal of the sensor from the target fiber causing the propagating WGMs to completely dissipate. The sensor is subsequently brought in contact at another location along the length of the fiber, initiating the creating of WGMs at this new location. This discrete contact approach has been found to overcome the microparticle collection and stick-slip problems of the sliding method of the prior art that had led to inaccurate measurements.

Thus, in another aspect, the present invention includes a method for characterizing local variations in optical fiber radius comprising the steps of: a) contacting an outer surface of an optical fiber at a first location with a microfiber sensor to create whispering gallery mode (WGM) resonances within a bounded region on either side of the first location; b) evaluating asymmetric Airy functions associated with a WGM resonance; and c) calculating a local slope γ of the optical fiber from the evaluated WGM resonance, the local slope defining a local variation in radius.

Other and further aspects of the present invention will become apparent during the course of the following description and by reference to the accompanying drawings.

BRIEF DESCRIPTION OF THE DRAWINGS

Referring now to the drawings,

FIG. 6(a)-(d) each contains a plot of the local WGM resonances associated with points a and b of FIG. 5, where FIG. 6(a) is the resonance associated with point a (and FIG. 6(c) is an enlargement of an area surrounding a specific resonance peak) and FIG. 6(b) is the resonance associated with point b (and FIG. 6(d) is an enlargement of an area surrounding a specific resonance peak);

FIGS. 8(a) and (b) each contain a plot of the local WGM resonances associated with separate locations along the test fiber of FIG. 7, where

DETAILED DESCRIPTION

Figure 1:
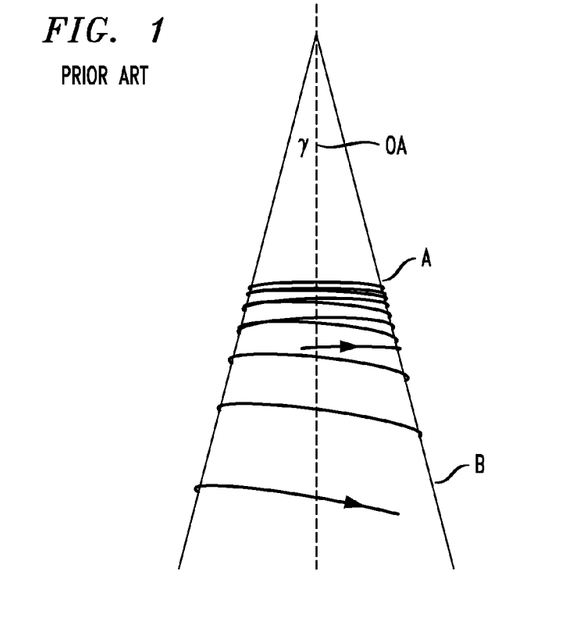
FIG. 1 is a prior art diagram of the conventional theory of the unbounded propagation of a ray along a conic section

Classical optics had previously concluded that all whispering gallery modes (WGMs) launched in a conical waveguide will be delocalized and continue to propagate in unbounded fashion, as shown in FIG. 1. That is, it would be expected that the motion is bounded on the narrower side A of the cone, and unbounded on the wider side B, so that any geodesic (classical ray) propagating at the conical surface will eventually move off to infinity.

Figure 2:
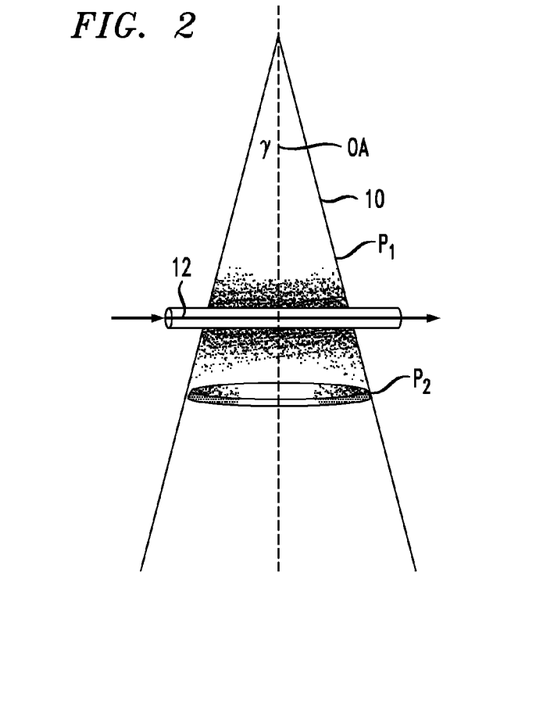
FIG. 2 is a diagram illustrated the finding of the present invention regarding the localization of a ray along a conic section with a relatively small half-angle γ.

Contrary to this premise of classical optics, however, it has been discovered that a conic section with a proper half-angle dimension is indeed bounded and is capable of supporting WGMs. In particular, for a cone with a relatively small half-angle γ (e.g., $\gamma < 10^{-2}$), a wave beam launched in a direction normal to the cone axis (such as from a sensor fiber for the case where the cone is defined as the target fiber) can be completely localized, as shown in FIG. 2. FIG. 2 illustrates an exemplary cone 10 with half-angle γ defined as shown and defining the slope of cone 10. A sensor fiber 12 is shown as positioned normal to optical axis OA of cone 10, where an optical signal propagating along sensor fiber 12 will excite WGMS within cone 10 upon contact between the two elements. The excited WGMs are shown as bounded (localized) at locations $P_1$ and $P_2$ on either side (above and below) the launch location (defined as a point z=0 along the optical axis).

Figure 3:
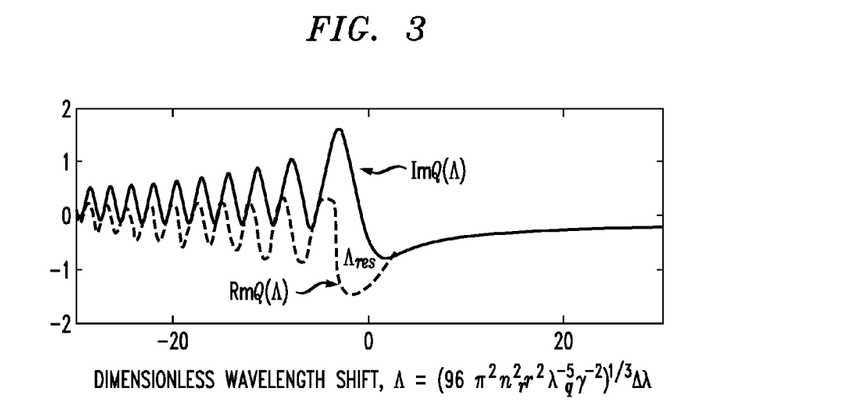
FIG. 3 is a plot of the transmission resonance shape of a conical WGM, exhibiting well-known asymmetric Airy-type oscillations.

It has been found that the transmission resonance shape of a conical WGM exhibits asymmetric Airy-type oscillations, as shown in FIG. 3. In accordance with the present invention, the measurement of these oscillations determines the local half-angle γ (which is also a measurement of the local slope) a slightly nonuniform microcylinder (e.g., optical fiber). Unlike the prior art methods, therefore, the method of the present invention is able to determine the local slope of an optical fiber from a single measurement. As the cone half-angle (or effective half-angle) decreases, the size of the localized mode grows very slowly, on the order of $\gamma^{-1/3}$. As described in detail below, this realization provides a unique approach for extremely accurate local characterization of optical fibers (which usually have γ of approximately $10^{-4}$ or less) and a new paradigm in the field of high Q-factor resonators. Indeed, by virtue of utilizing the conical microresonator approach of the present invention, angstrom-level variations in optical fiber radius during the manufacturing process can be monitoring and controlled, improving the quality of the produced optical fiber. Additionally, the present invention allows measurement, detection or exploitation of any effect that modifies the effective radius of the optical fiber. The need to only perform a single measurement to determine the local slope of an optical fiber being tested—as opposed to the prior art sliding technique that requirement multiple measurements—results in improving the efficiency of the measurement process. As will be discussed below, the technique of the present invention is best implemented when multiple spectral resonance peaks are monitored as a "group"—as opposed to the prior art approach of watching the movement of a single peak as the sensor fiber is slid along the target fiber.

Figure 4:
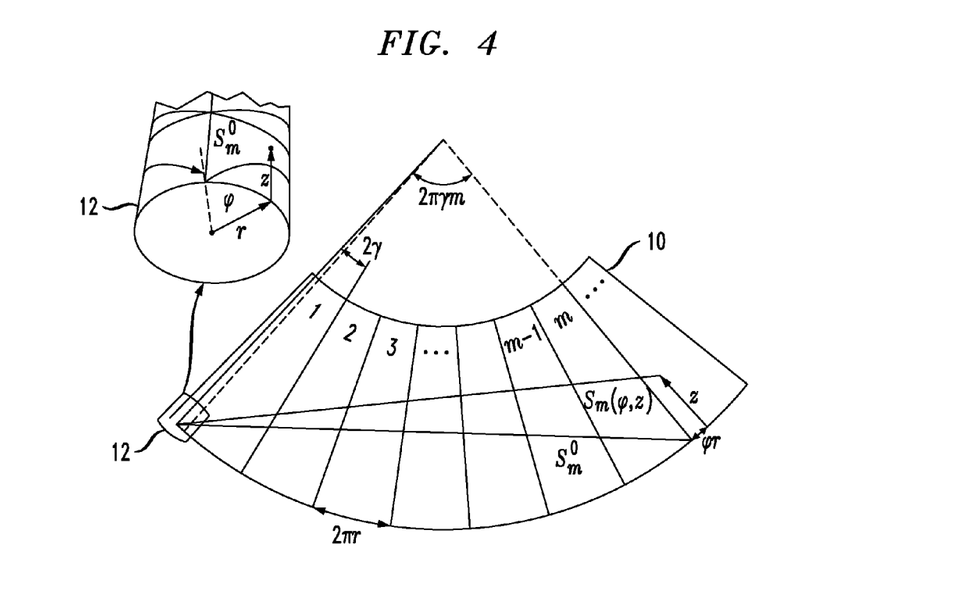
FIG. 4 is an "unfolded" view of the conic section of FIG. 2, illustrating the propagation of rays after multiple turns around the circumference of the conic section.

The geometry of light propagating along the conical surface of cone 10 of FIG. 2 can best be visualized in the configuration of FIG. 4, where cone 10 has been "unfolded" into a planar form. Thus, when considering the planar structure of FIG. 4, all of the conical geodesics experiencing multiple turns around the circumference of cone 10 are transformed into straight lines. Similarly, a light beam propagating along a curved geodesic at the surface of cone 10 is transformed into a beam that diffracts in the vicinity of a straight line at the unfolded surface.

A beam launched in the vicinity of the physical contact point between sensor 12 and cone 10 ($\phi=z=0$, where $\phi$ is the azimuthal angle and z is the fiber axial coordinate, as shown in the inset of FIG. 4) can be expanded into a linear combination of planar Gaussian beams of order n having the following form:

$$(is_0+s)^{-\frac{n}{2}} H_n\left[\beta^{\frac{1}{2}} z(is_0+s)^{-\frac{1}{2}}\right] \exp[i(\beta+i\alpha)s],$$

where $\beta$ and $\alpha$ are the propagation and attenuation constants, respectively, $H_n(x)$ is a Hermite polynomial, $s_0$ defines the beam waist at the launch point and $s=s(\phi,z)$ is the distance between the original point $\phi=z=0$ and a given point $(\phi,z)$ calculated along the unfolded conical surface of FIG. 4.

After a number of turns m (i.e., a large distance s on the unfolded view), the beams with n>0 vanish as $s^{-(n+1)/2}$ and become negligible compared to the fundamental Gaussian beam with n=0. Additionally, the waist parameter $s_0$ can be neglected for large values of s. Therefore, for a weak microfiber/cone coupling (i.e., in the strongly undercoupling regime), the resonant field $\psi$ at point $(\phi,z)$ of the cone surface is found as the superposition of fundamental Gaussian beams that are launched at point $\phi=z=0$ and make m turns before approaching point $(\phi,z)$:

$$\Psi(\varphi,z) \sim \sum_m S_m(0,0)^{-\frac{1}{2}} \exp[i(\beta+i\alpha)S_m(\varphi,z)],$$

where $S_m(\phi,z)$ is defined as the distance between the launch point and point $(\phi,z)$ calculated along the geodesic that connects these points after completing m turns (see FIG. 4). Therefore, it follows from FIG. 4 that for $2\pi m\gamma \ll 1$, the distance $S_m(\phi,z)$ can be simplified as follows:

$$S_m(\phi,z) \approx S_m^0 + \phi r - \pi m\gamma z + z^2/(2S_m^0),$$

where r is the local cone radius of the circumference $(\phi,0)$ and $S_m^0$ is the length of the geodesic crossing itself at the original point after m turns (see FIG. 4):

$$S_m^0 = \frac{2r}{\gamma} \sin(\pi\gamma m) \approx 2\pi rm - \frac{\pi^3}{3}\gamma^2 rm^3.$$

The resonance propagation constant $\beta_q$ can be defined by the quantization condition along the circumference $(\phi,0)$: $\Theta_q=q/r$, where q is a large integer. Assuming that the sum defined above is determined by terms with large number $m \gg 1$, it may be replaced by an integral, and the resonant field can be re-defined as follows:

$$\Psi(\varphi,t) \sim \exp(iq\varphi)$$

$$\int_0^\infty \frac{dm}{m^{1/2}} \exp\left\{\pi i[2(\Delta\beta+i\alpha)r-\beta_q\gamma z]m - \frac{i\pi^3\beta_q}{3}\gamma^2 rm^3 + \frac{i\beta_q z^2}{4\pi rm}\right\},$$

where $\Delta\beta=\beta-\beta_q$ is the deviation of the propagation constant. In this expression, the first term in the square brackets and the last term in the exponent correspond to the usual Gaussian beam propagating along a straight line. The terms proportional to $\gamma^2 m^3$ and $\gamma m$ characterize the curved geodesic and are responsible for the major effects described in detail below.

Indeed, the above equation for the resonant field is valid if the deviation of the propagation constant $\Delta\beta$, attenuation $\alpha$ and cone slope $\gamma$ are small, that is, if $\Delta\beta, \alpha \ll (2\pi r)^{-1}$, and $$\gamma \ll \pi^{-3/2} (\beta r)^{-1/2}.$$

This limitation on the definition of the cone slope (or effective slope $\gamma_{eff}$) is thus used in accordance with the present invention to define the type of conic section that will support WGM resonances. For a conventional optical fiber of radius $r\sim50$ μm and effective refractive index $n_r\sim1.5$ that is used to support the propagation of an optical signal at a wavelength $\lambda$ of about 1.5 μm, it follows that $\beta=2\pi n_r/\lambda \sim 6$ μm$^{-1}$ and the above constraint is satisfied for $\gamma \ll 10^{-2}$.

If the microfiber/cone coupling is localized near $\phi=z=0$, then the resonant transmission power is found from the above relations as $P=|1-D-C\Psi(0,0)|^2$, where the parameters D and C are constants in the vicinity of the resonance. For the case of weak coupling as considered here, $|D| \ll 1$ and $|C\Psi(0,0)| \ll 1$, so that $$P \approx 1 - 2\mathrm{Re}(D) - 2\mathrm{Re}\left\{C\int_0^\infty \frac{dm}{m^{1/2}} \exp\left[2\pi r(i\Delta\beta-\alpha)m - \frac{i\pi^3\beta_q}{3}\gamma^2 rm^3\right]\right\}.$$

From this, there are two possibilities. For a relatively small cone half-angle, $\gamma \ll 5\alpha^{3/2}\beta^{-1/2}r$, the terms depending on $\gamma$ in the exponents can be neglected and the conical resonator of the present invention behaves as a uniform cylindrical resonator as studied in the prior art. Alternatively, if $\gamma \gg 5\alpha^{3/2}\beta^{-1/2}r$, the effect of loss is suppressed by the slope value $\gamma$ and the term $\alpha$ can be neglected, defining the condition of "slope-defined resonance". In optical fibers, it is common that the attenuation $\alpha < 10^{-6}$ μm$^{-1}$. Then, for a conventional wavelength $\lambda$ of about 1.5 μm, effective refractive index $n_r\sim1.5$ and radius $r\sim50$ μm, the above condition for resonant transmission power is satisfied for $\gamma \gg 10^{-7}$. This experimental situation will be considered and discussed below.

Indeed, for the case of slope-defined resonance, the transmission power P is a linear combination of a constant with the real (Re) and imaginary (Im) parts of the integral $$P(\Lambda) = -\int_0^\infty x^{-1/2} \exp(i\Lambda x + ix^3) dx$$

depending on the dimensionless wavelength shift $\Lambda = (96\pi^2 n_r^2 r^2 \lambda_q^{-5} \gamma^{-2})^{1/3} \Delta\lambda$, where for convenience the resonance wavelength $\lambda_q = 2\pi n_r/\beta_q$ and wavelength shift $\Delta\lambda=\lambda-\lambda_q$ are introduced. The plots of the real and imaginary parts of function $P(\Lambda)$ are known as the generalized Airy function, as shown in the plots of FIG. 3. Similar to the ordinary Airy function, this function has asymmetric oscillations vanishing away from the principal peak. The dimensionless width of this peak, $\Lambda_{res} \approx 5$, corresponds to the characteristic width of the principal spectral resonance:

$$\Delta\lambda_{res} \approx 0.5 n_r^{-\frac{2}{3}} \lambda^{\frac{5}{3}} \lambda^{\frac{2}{3}} r^{-\frac{2}{3}}.$$

For small slopes $\gamma$, the value $\gamma\lambda_{res}$ decreases as $\gamma^{2/3}$ and defines the limit of the spectral resolution. For example, for an optical fiber radius $r\sim50$ μm, wavelength $\lambda\sim1.5$ μm, refractive index $n_r\sim1.5$ and fiber slope $\gamma\sim10^{-5}$, the characteristic width of the principal spectral resonance $\Delta\lambda_{res}$ is on the order of 23 pm. In this case, therefore, the identification of the resonance structure in the functions shown in FIG. 3 requires a pm wavelength resolution.

It has been found that the characteristic size of the localized conical mode is defined as follows:

$$z_{res}=(2\pi n_r)^{-2/3}(3\lambda)^{2/3}r^{1/3}\gamma^{-1/3}.$$

The $\gamma^{-1/3}$ dependence is very slow; thus, it has been determined in accordance with the present invention that a conical resonator with an extremely small slope (i.e., half-angle) $\gamma$ can support strongly localized states. In fact, for the above example, $z_{res}$ is approximately 100 μm.

In order to experimentally verify the described theory, the transmission spectra at two positions of a 50 mm fiber segment (radius r of approximately 76 μm) were examined to directly determine variations in radius, where these direct measurements were then compared to variations in radius determined from evaluation of the resonances in accordance with the present invention.

Figure 5:
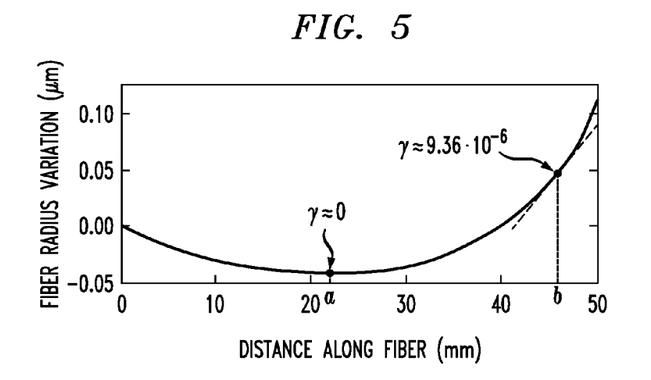
FIG. 5 is a graph of directly measured radius variations for an exemplary optical fiber.

The first step, therefore, was to directly measure the variation in radius of the fiber segment as a function of length. FIG. 5 is a plot of this directly measured radius variation. To perform this measurement, a microfiber test probe was positioned perpendicularly to the fiber segment, where an optical signal propagating along the test probe would then be evanescently coupled into the fiber segment and produce WGMs (such as shown in FIG. 2). The resonant transmission spectra were measured at points spaced by 2 mm along the fiber segment in the wavelength interval between 1535 nm and 1545 nm. The coupling between the microfiber test probe and the fiber segment was tuned to small values by shifting the contact point to a thicker part of the microfiber.

To produce the plot of FIG. 5, the radius variation Δr was calculated from the shift of resonance positions, Δλ, since Δr=λΔλ/r. Referring to FIG. 5, two specific measurement locations were defined, with point a defining a location where there was essentially no local variation in radius (slope $\gamma$ being essentially 0) and point b defining a location where there was significant variation (slope $\gamma$ having a relatively large positive value of about $9.36 \cdot 10^{-6}$.

Figure 6:
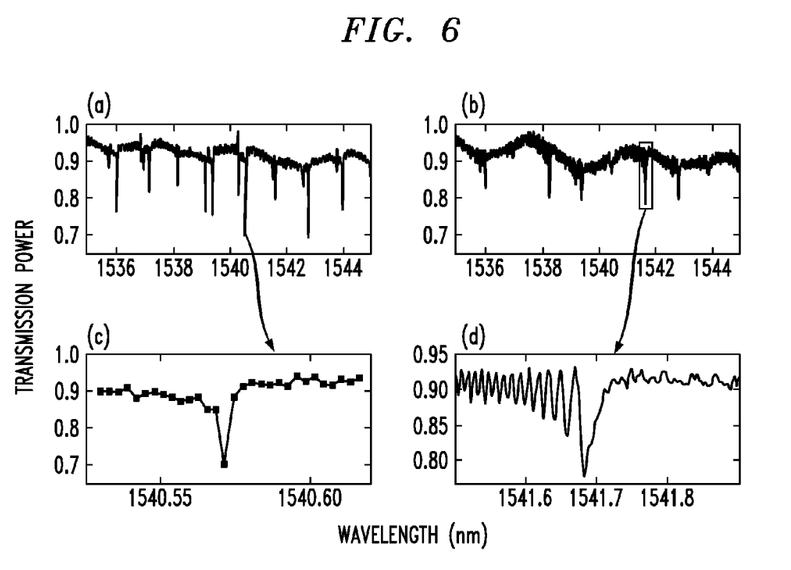

Once these directly measured values were obtained, it was possible to use the WGM resonances evaluation characterization technique of the present invention to theoretically predict the slope value $\gamma$ and analyze the agreement between the measured and predicted values. FIG. 6(a)-(d) each contains a plot of the local WGM resonances associated with points a and b of FIG. 5, where FIG. 6(a) is the resonance associated with point a (and FIG. 6(c) is an enlargement of an area surrounding a specific resonance peak centered near 1540.5 nm) and FIG. 6(b) is the resonance associated with point b (and FIG. 6(d) is an enlargement of an area surrounding a specific resonance peak centered near 1541.7 nm).

In particular, the transmission spectra at points a and b were examined and the WGMs evaluated. For point a, the corresponding transmission resonant spectrum is shown in FIG. 6(a). Since the change in radius is negligible at this point ($\gamma$ essentially zero), the transmission spectrum is determined primarily by the WGM attenuation α. At this position, the characteristic resonance width is smaller than the measurement resolution (see the magnified resonance sample in FIG. 6(c)), allowing the estimation of the attenuation constant as $\alpha<10^{-6}$ um$^{-1}$.

At the second position (point b), the variation in radius found by direct measurement suggested that the resonant transmission spectrum should exhibit the characteristic asymmetric oscillating behavior (Airy function) described above and shown in FIG. 3. FIG. 6(b) is the transmission resonant spectrum associated with point b, with a magnified structure of a single resonance peak shown in FIG. 6(d). Clearly, FIG. 6(d) exhibits this expected asymmetric Airy function form and therefore confirms the prediction that the WGMs are indeed bounded in a conic section and the inventive theory is a valid characterization of local variation of fiber radius. The experimental data for point b in FIG. 6(b) and (d) can be fit by the linear combination of Re P(Λ) and Im P(Λ), assuming r~76 μm, λ=1.54 μm and $n_r$=1.46, resulting in $\gamma \sim 9.354 \cdot 10^{-6}$ with better than 0.1% accuracy. This value is remarkably close to the directly-measured slope value of $\gamma \approx 9.36 \cdot 10^{-6}$.

The results of the experiments as particularly exemplified in the resonance plot of FIG. 6(d) thus strongly support the theory of the present invention that a conical optical resonator can be created and will support WGMs exhibiting the characteristic asymmetric oscillating behavior (Airy function).

As discussed above, the problem of accurately measuring radius variation of an optical fiber is important for applications such as, for example, characterization of fiber transmission properties, inscription of Bragg gratings, and the like. Indeed, several applications require extremely accurate measurement of the fiber radius variation at the angstrom scale. Prior art methods consist of the excitation of WGMs using a microfiber test probe, with the probe then sliding along the fiber being measured. However, in the application of such prior art methods, it was found that the shape of the WGM resonances was quite complex and contained numerous peaks. It was not clear how to treat the shape of the WGM resonances and the variations in order to restore the fiber radius variation. Further, the physical reason for the shape of these WGM resonances was not understood.

Now, with the understanding of the present invention in terms of the ability of a conic section to support WGMs in the form of asymmetric Airy functions, a method is established that defines the relationship between the local shape of an optical fiber and its associated WGM transmission resonances. This relationship can be generalized to also include the local variation of the refractive index of the fiber. An embodiment of this method of the present invention, as described below, allows for the determination of fiber radius variations from the shape and other properties of the WGM transmission resonances. A further embodiment of this method of the present invention allows for the determined of the effective fiber radius variation, or the refractive index variation, from the shape and other properties of the WGM transmission resonances. In particular, a discrete contact method of touching a target fiber with a localized optical source such as a microfiber sensor provides for robust and angstrom-scale measurement of the radius variation along the length of the target fiber. The described method determines the radius variation without the need for visual recognition of resonances (or monitoring changes/shifts in a single resonance); rather, multiple resonances are utilized and their shifts are treated simultaneously.

Figure 7:
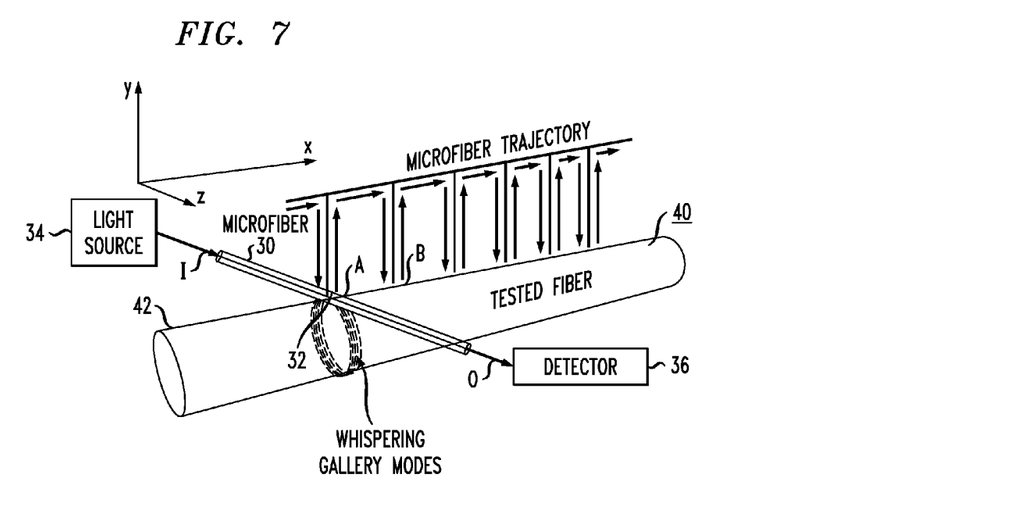
FIG. 7 depicts an exemplary configuration for implementing a "touch and go" method of measuring radius variations along an optical fiber.

FIG. 7 illustrates an exemplary arrangement that demonstrates the optical fiber characterization principle of the present invention. In this particular embodiment, a biconical fiber taper 30 (hereinafter referred to as a microfiber sensor 30), having a diameter on the order of 1.3 μm and a tapered waist region 32, is used as the localized optical source and receives an input optical test signal I from a light source 34 (preferably, a tunable laser source). Other types of localized optical sources may be used including, but not limited to, planar optical waveguides and free space propagating optical signals (a free space signal needing to be focused so as to evanescently couple into the optical fiber being tested). It is to be understood that methods of detection are to be compatible with the resolution of the spectral resonant peaks in the output spectra, where one method of detection utilizes an optical spectrum analyzer (if a suitably broadband signal source is used) or a power meter (if a narrow linewidth tunable source is used).

Referring back to FIG. 7, a detector 36 is positioned to receive the output signal O from microfiber sensor 30. A nominally "uniform radius" and "uniform index" optical fiber 40 is being tested in the example, where microfiber sensor 30 is positioned to contact optical fiber 40 in an approximately normal (perpendicular) orientation that will encourage excitation of WGMs within optical fiber 40. The actual point of contact between microfiber sensor 30 and optical fiber 40 is controllable by the user; while the point of contact is presumably within the area of tapered waist region 32, the disposition of the two elements can controlled so as to increase or decrease, as desired, the amount of optical signal power evanescently coupled into optical fiber 40.

In order to perform a series of measurements along the length of optical fiber 40, a series of discrete contacts are performed, where microfiber sensor 30 is first positioned to contact outer surface 42 of optical fiber 40 at a first point A. Microfiber sensor 30 is then removed from this contact site, such that contact between sensor 30 and the optical fiber 40 is broken, and re-positioned to contact optical fiber 40 at a second point B, and so on. In one embodiment, a pair of linear orthogonal stages x and y (not shown) may be used to direct the movement of microfiber sensor 30 along axes x and y, respectively. At all times, microfiber sensor 30 remains aligned along the z-axis of optical fiber 40, as shown in FIG. 7.

Figure 8:
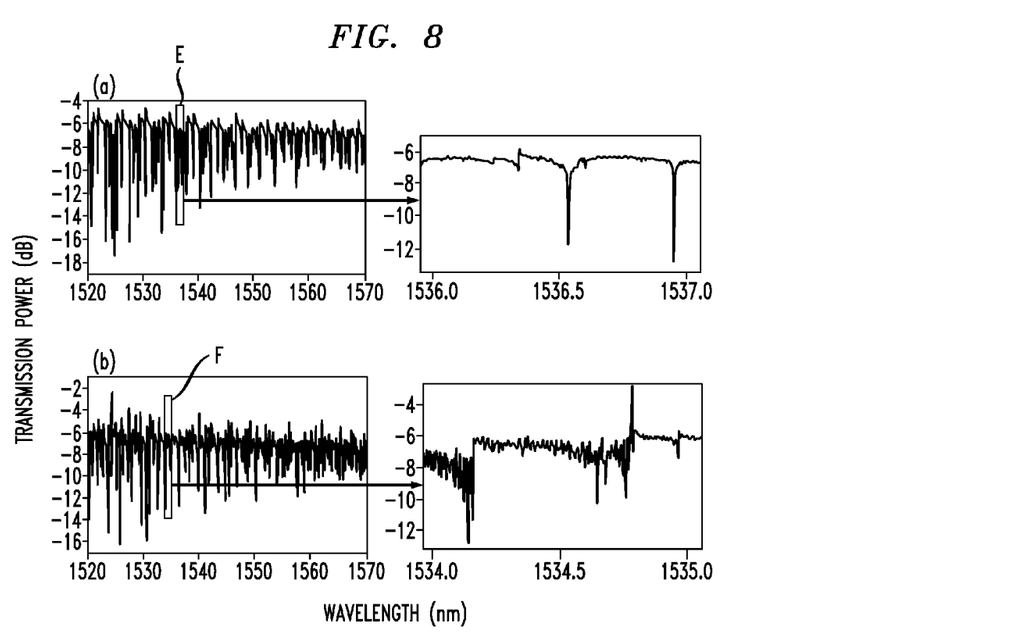
FIG. 8(a) illustrates the resonance associated with first location (also showing an enlargement of an area E surrounding a specific resonance peak) and FIG. 8(b) is the resonance associated with second, separate location (also showing an enlargement of an area F surrounding a specific resonance peak)

At each of the contacts along points A, B, etc., a WGM resonance transmission spectrum is created and is measured by detector 36. Two exemplary resonance spectra are shown in FIGS. 8(a) and (b). Enlargements surrounding selected resonance peaks are also shown, where in FIG. 8(a) an enlargement of area E is shown and in FIG. 8(b) an enlargement of area F is shown. As discussed in detail above, for cases where the fiber half-angle $\gamma < 10^{-2}$, these spectra take the form of asymmetric Airy functions and provide information regarding the local variation in radius. The plots of FIG. 8(b) are indicative of a location along optical fiber 40 where such a variation is present.

In prior art measurement techniques, a single resonance peak $\lambda$ would be "defined" at a first measurement point (such as point A), and variations in this resonance ($\Delta\lambda$) as occurring along the length of the fiber (as the sensor was slid along the fiber in a continuous contact arrangement) used to indicate the presence of variations in radius (with $\Delta r$ as defined above). However, it would happen that a selected resonance would "disappear" or seriously degrade during the course of the measurement process, resulting in the need to select a different peak and repeat the entire measurement process.

In accordance with this aspect of the present invention, a simple and general method of simultaneously evaluating several resonances is provided that addresses and overcomes the problems associated with the conventional prior art method of measuring only a single resonance peak.

In particular, at each measurement step n (such as, points A, B, etc.), wavelength coordinates of M resonances are selected for evaluation, $\lambda_m^{(n)}$, m=1, 2, . . . , M. As noted above, the effective radius variation $\Delta r$ is calculated as from the shift of a given resonance peak, $\Delta\lambda$, where $\Delta r = \lambda \Delta\lambda / r$. Taking this definition one step further, it is now defined that the radius variation $\Delta r = \Delta r_n$ between the measurement steps n and (n−1) is found by maximizing the following goal function:

$$M_n^{(G)}(\Delta r) = \sum_{m_1=1}^{M} \sum_{m_2=1}^{M} \exp\left(-\frac{1}{\xi^2}\left|\lambda_{m_1}^{(n-1)} - \lambda_{m_2}^{(n)} - \frac{\lambda_{m_2}^{(n)}}{r}\Delta r\right|^2\right),$$

where the parameter $\xi$ determines the resolution required for the wavelength shift.

This maximized goal function $M_n^{(G)}(\Delta r)$ has a clear physical meaning with respect to the fiber being tested. In particular, assume that the maximization of this function yields $M_n$ resonances for which the value $\Delta r_n$ is determined with an accuracy better than $\xi r/\lambda$, while the shifts associated with the remaining M−$M_n$ resonances ($|\lambda_{m_1}^{(n-1)} - \lambda_{m_2}^{(n)}|$) are significantly greater than $\xi$. In this event, $M_n^{(G)}(\Delta r)$ determines the number of resonances corresponding to the radius variation $\Delta r = \Delta r_n$, i.e., $M_n^{(G)}(\Delta r) \approx M_n$. In general, the value $M_n^{max} = M_n^{(G)}(\Delta r_n)$ as compared to the total number of considered resonances M is an important characteristic of the measurement quality.

Figure 9:
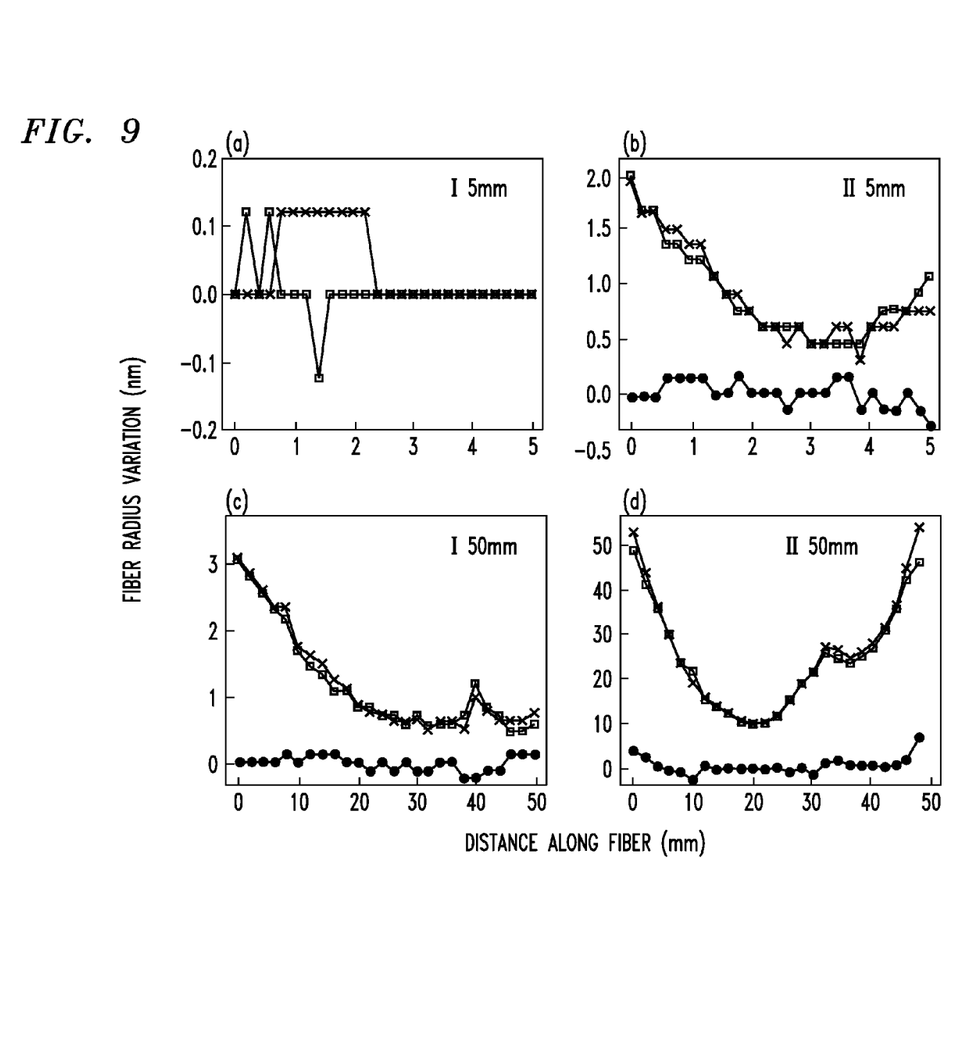
FIG. 9 illustrate variations in fiber radius for two different fibers, measured using the arrangement of FIG. 7.

The novel measurement process of the present invention was applied to provide a characterization of two different optical fibers, denoted as fiber I and fiber II. FIG. 9 shows the radius variation measured for fiber I with a nominal radius r=62.5 μm, and for fiber II with a nominal radius r=76.5 μm. These fibers I and II were fabricated under different conditions, so it is a fair presumption that their characteristics will be different.

The procedure of the present invention was applied to measurement data taken along the wavelength interval $\lambda = 1520$ nm to $\lambda = 1570$ nm, for M=40 and a resolution of $\xi = 3$ pm. The $M_n^{max}$ varied between values of 35 and 9 for each measurement point. Referring to FIG. 9, it was found that fiber I was characterized by a small and smooth radius variation, while fiber II was characterized by a much larger radius variation.

FIGS. 9(a) and (b) compare two separate radius variation measurements (shown by x's and □'s) for the same 5 mm segment of each of fibers I and II, with an incremental step size of 200 μm between measurements. It is to be noted that the ordinates of the plots of FIGS. 9(a) and (b) differ in scale by a factor of 10, with the difference between the two measurements along fiber II shown in the lower region of FIG. 9(b). These plots suggest that angstrom accuracy in fiber radius measurement is achievable with the method of the present invention. Similarly, FIGS. 9(c) and (d) show the radius variation of the same fibers I and II as measured along 50 mm segments, with incremental steps of size 2 mm. While the variation of radius for fiber I is very smooth and exhibits a value close to about 1 nm, the variation in radius for fiber II is much larger, on the order of 50 nm, and is noticeably less smooth. Thus, it is clear that the angstrom-level accuracy of the method of the present invention in determining variations in the radius of an optical fiber is a practical, non-invasive technique for controlling the quality of a optical fiber as it is being manufactured or qualified for a particular use. Heretofore, it was difficult—if not impossible—to repeatedly and accurately measure angstrom variations in optical fiber radius.

It is to be noted that an optical fiber with extremely small and smooth nonuniformities can be assumed to be locally uniform. For such a fiber, the observed resonances are approximately described by the theory of WGMs in a uniform cylinder.

While specific examples of the invention are described in detail above to facilitate explanation of various aspects of the invention, it should be understood that the intention is not to limit the invention to the specifics of the examples. Rather, the intention is to cover all modifications, embodiments and alternatives falling within the spirit and scope of the invention as defined by the appended claims.

What is claimed is:

1. A high Q-factor optical microresonator comprising
a conical optical waveguide having a half-angle $\gamma$, where to support localized whispering gallery modes (WGMs), $\gamma$ satisfies the relation:

$$\gamma \ll \pi^{-3/2}(\beta r)^{-1/2},$$

where r is defined as the local radius of the conical optical waveguide and $\beta$ is a propagation constant defined by $\beta=2\pi n_r/\lambda$, with $\lambda$ defined as an optical signal propagating along an optical axis of the optical microresonator and $n_r$ defined as the refractive index of the conical optical waveguide; and
    a localized optical source disposed in contact with the conical optical waveguide, wherein the localized optical source is used for excitation of WGMs in the conical optical waveguide.

2. A high Q-factor optical microresonator as defined in claim 1 wherein the localized optical source is an optical microfiber oriented normal to the optical axis of the optical microresonator.

3. A high Q-factor optical microresonator as defined in claim 2 wherein the optical microfiber comprises a tapered waist region for contacting the conical optical waveguide.

4. A high Q-factor optical microresonator as defined in claim 1 wherein the localized optical source is a planar optical waveguide.

5. A high Q-factor optical microresonator as defined in claim 1 wherein the localized optical source is a free space optical signal that is focused to evanescently couple into the conical optical waveguide.

6. A high Q-factor optical microresonator as defined in claim 1 where the conical optical waveguide comprises a section of optical fiber.

7. A high Q-factor optical resonator as defined in claim 1 wherein the conical optical waveguide exhibits an effective conical angle $\gamma_{eff}$, defined as follows:

$$\gamma_{eff} = \gamma + \gamma_{ind}(r/n_0),$$

wherein $\gamma_{ind}$ is the slope of the index variation and $n_0$ is the refractive index of the optical microresonator.

* * * * *